United States Patent
Silverman et al.

(10) Patent No.: US 11,376,112 B2
(45) Date of Patent: Jul. 5, 2022

(54) PRE-STRAINED STENT ELEMENTS

(71) Applicant: W. L. Gore & Associates, Inc., Newark, DE (US)

(72) Inventors: James D. Silverman, Flagstaff, AZ (US); Olga Baykova, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/481,193

(22) PCT Filed: Jan. 29, 2018

(86) PCT No.: PCT/US2018/015736
§ 371 (c)(1),
(2) Date: Jul. 26, 2019

(87) PCT Pub. No.: WO2018/144387
PCT Pub. Date: Aug. 9, 2018

(65) Prior Publication Data
US 2019/0388214 A1   Dec. 26, 2019

Related U.S. Application Data

(60) Provisional application No. 62/452,771, filed on Jan. 31, 2017.

(51) Int. Cl.
*A61F 2/07* (2013.01)

(52) U.S. Cl.
CPC ........ *A61F 2/07* (2013.01); *A61F 2250/0018* (2013.01); *A61F 2250/0039* (2013.01)

(58) Field of Classification Search
None
See application file for complete search history.

(56) References Cited

U.S. PATENT DOCUMENTS

| 3,953,566 A | 4/1976 | Gore |
| 4,187,390 A | 2/1980 | Gore |
| 4,503,569 A | 3/1985 | Dotter |

(Continued)

FOREIGN PATENT DOCUMENTS

| JP | 2003-505144 A | 2/2003 |
| JP | 2005-514968 A | 5/2005 |

(Continued)

OTHER PUBLICATIONS

International Preliminary Reporton Patentability received for PCT Patent Application No. PCT/US2011/065989, dated Jul. 4, 2013, 5 pages.

(Continued)

*Primary Examiner* — Leslie Lopez

(57) ABSTRACT

Various aspects of the present disclosure are directed toward apparatuses, systems and methods that include a self-expanding endoprosthesis having a reduced configuration and a deployed configuration. The self-expanding endoprosthesis may include a self-expanding stent element having an enlarged diameter and a graft component attached to at least a portion of the self-expanding stent element and having an enlarged diameter less than the enlarged diameter of the self-expanding stent element in the deployed configuration.

15 Claims, 8 Drawing Sheets

(56) References Cited

U.S. PATENT DOCUMENTS

| | | | |
|---|---|---|---|
| 4,512,338 | A | 4/1985 | Balko et al. |
| 4,990,155 | A | 2/1991 | Wilkoff |
| 5,037,427 | A | 8/1991 | Harada et al. |
| 5,147,370 | A | 9/1992 | McNamara et al. |
| 5,211,658 | A | 5/1993 | Clouse |
| 5,221,261 | A | 6/1993 | Termin et al. |
| 5,276,276 | A | 1/1994 | Gunn |
| 5,922,019 | A | 7/1999 | Hankh et al. |
| 6,042,602 | A | 3/2000 | Wells |
| 6,086,610 | A | 7/2000 | Duerig et al. |
| 6,110,198 | A | 8/2000 | Fogarty et al. |
| 6,120,534 | A | 9/2000 | Ruiz |
| 6,139,573 | A | 10/2000 | Sogard et al. |
| 6,203,735 | B1 | 3/2001 | Edwin et al. |
| 6,336,937 | B1 * | 1/2002 | Vonesh .............. A61F 2/07 623/1.13 |
| 6,352,561 | B1 | 3/2002 | Leopold et al. |
| 6,355,057 | B1 | 3/2002 | Demarais et al. |
| 6,366,937 | B1 | 4/2002 | Shridhar et al. |
| 6,395,212 | B1 | 5/2002 | Solem |
| 6,402,779 | B1 | 6/2002 | Colone et al. |
| 6,551,350 | B1 | 4/2003 | Thornton et al. |
| 6,613,077 | B2 | 9/2003 | Gilligan et al. |
| 6,635,083 | B1 | 10/2003 | Cheng et al. |
| 6,729,356 | B1 | 5/2004 | Baker et al. |
| 6,773,454 | B2 | 8/2004 | Wholey et al. |
| 6,899,727 | B2 | 5/2005 | Armstrong et al. |
| 6,981,982 | B2 | 1/2006 | Armstrong et al. |
| 7,049,380 | B1 | 5/2006 | Chang et al. |
| 7,731,744 | B1 | 6/2010 | Cox |
| 8,048,138 | B2 | 11/2011 | Sullivan et al. |
| 2001/0039446 | A1 * | 11/2001 | Edwin .............. A61F 2/07 623/1.13 |
| 2001/0053929 | A1 | 12/2001 | Vonesh et al. |
| 2002/0007955 | A1 | 1/2002 | Wiens |
| 2002/0177891 | A1 | 11/2002 | Parodi |
| 2004/0063805 | A1 | 4/2004 | Pacetti et al. |
| 2005/0049667 | A1 | 3/2005 | Arbefeuille et al. |
| 2006/0052865 | A1 | 3/2006 | Banas |
| 2006/0198866 | A1 | 9/2006 | Chang et al. |
| 2008/0039927 | A1 | 2/2008 | Barr |
| 2008/0071356 | A1 | 3/2008 | Greenhalgh et al. |
| 2008/0288044 | A1 | 11/2008 | Osborne |
| 2009/0048662 | A1 | 2/2009 | Pavcnik et al. |
| 2012/0323304 | A1 | 12/2012 | Buckley et al. |
| 2013/0131780 | A1 | 5/2013 | Armstrong et al. |
| 2015/0005870 | A1 | 1/2015 | Kovach et al. |
| 2020/0289254 | A1 | 9/2020 | Buckley et al. |

FOREIGN PATENT DOCUMENTS

| | | |
|---|---|---|
| JP | 2007-503923 A | 3/2007 |
| WO | 97/33532 A2 | 9/1997 |
| WO | 98/26731 A2 | 6/1998 |
| WO | 01/06953 A1 | 2/2001 |
| WO | 01/24733 A1 | 4/2001 |
| WO | 2002/100297 A2 | 12/2002 |

OTHER PUBLICATIONS

International Preliminary Report on Patentability received for PCT Patent Application No. PCT/US2018/015736, dated Aug. 15, 2019, 7 pages.

International Search Report and Written Opinion received for PCT Patent Application No. PCT/US2011/065989, dated Jun. 26, 2012, 7 pages.

International Search Report and Written Opinion received for PCT Patent Application No. PCT/US2018/015736, dated Apr. 17, 2018, 10 pages.

* cited by examiner

PRE-STRAINED STENT ELEMENTS

CROSS-REFERENCE TO RELATED APPLICATION

This application is a U.S. 371 Application of International Application PCT/US2018/015736, filed Jan. 29, 2018, which claims the benefit of U.S. Provisional Application No. 62/452,771, filed Jan. 31, 2017, both of which are herein incorporated by reference in their entirety.

BACKGROUND

Medical stents, grafts, and stent-grafts have a variety of uses including to expand a body lumen, such as a blood vessel, which has contracted in diameter. The blood vessels may be diseased, contracted or otherwise damaged due to, for example, the effects of lesions called atheroma or the occurrence of cancerous tumors. Atheroma refers to lesions within arteries that include plaque accumulations that can obstruct blood flow through the vessel. Over time, the plaque can increase in size and thickness and can eventually lead to clinically significant narrowing of the artery, or even complete occlusion. When expanded against the body lumen, which has contracted in diameter, the medical stents provide a tube-like support structure inside the body lumen. Additional, non-limiting examples of stent, graft and/or stent-graft applications include the endovascular repair of aneurysms, an abnormal widening or ballooning of a portion of a body lumen which can be related to weakness in the wall of the body lumen.

SUMMARY

Various aspects of the present disclosure are directed toward self-expanding endoprosthesis having a reduced configuration and a deployed configuration. The self-expanding endoprosthesis may include a self-expanding stent element having an enlarged diameter and a graft component attached to at least a portion of the self-expanding stent element and having an enlarged diameter less than the enlarged diameter of the self-expanding stent element in the deployed configuration. In addition and in the deployed configuration, the self-expanding stent element may exert a radially expansive force to the graft component. The graft component may have a yield strength greater than the radially expansive force and being configured to radially maintain the self-expanding stent element at the enlarged diameter of the graft component upon application of a second radially expansive force greater than the radially expansive force of the self-expanding stent element.

Aspects of the disclosure are also directed toward a self-expanding endoprosthesis having a self-expanding stent element with a manufactured diameter of from 7 mm to 32 mm and a graft component with an expanded diameter of from 5 mm to 27 mm. The self-expanding stent element may include a self-deployed diameter of is at least from 2% to 25% greater than the expanded diameter of the graft component. In addition, the expanding stent element may be attached at least in part to the graft component. Further, when the self-expanding endoprosthesis is fully deployed, the self-expanding stent element may continue to apply outward force against the graft component without expanding beyond the expanded diameter of the graft component.

Various aspects of the present disclosure are also directed toward a self-expanding endoprosthesis that include a self-expanding stent element having a neutral diameter of from 22 mm to 58 mm and a graft component with an expanded diameter of from 20 mm to 53 mm and attached to the self-expanding stent element. The self-expanding stent element and the graft component may be configured to reduce to a delivery configuration from a fully-deployed configuration for introduction into a patient. In addition, a self-deployed diameter of the self-expanding stent element may be at least from 2% to 25% greater than the expanded diameter of the graft component with the graft component being configured to maintain the self-expanding stent element at the expanded diameter of the graft component.

Aspects of the present disclosure are further directed toward a self-expanding endoprosthesis having a reduced configuration and a deployed configuration. The self-expanding endoprosthesis may include a self-expanding stent element having an enlarged diameter and a diametric constraint coupled to at least a portion of the self-expanding stent element. The diametric constraint may be configured to constrain the portion of the self-expanding stent to an enlarged diameter less than the enlarged diameter of the self-expanding stent element in the deployed configuration. In the deployed configuration, the self-expanding stent element may exert a radially expansive force to the graft component. In addition, the graft component may include a yield strength greater than the radially expansive force and being configured to radially maintain the self-expanding stent element at the enlarged diameter of the graft component upon application of a second radially expansive force greater than the radially expansive force of the self-expanding stent element.

Various aspects of the present disclosure are also directed toward a self-expanding endoprosthesis having a reduced configuration and a deployed configuration. The self-expanding endoprosthesis may include a self-expanding stent element having a manufactured diameter and an expanded diameter and a graft component attached to the self-expanding stent element and having an enlarged diameter less than the enlarged diameter of the self-expanding stent element in the deployed configuration. In addition, the self-expanding stent may be configured to exhibit plastic strain in response to being reduced to the reduced configuration and at the deployed diameter.

Various aspects of the present disclosure are also directed toward methods of manufacturing a self-expanding endoprosthesis having a reduced configuration and a deployed configuration. The methods may include reducing a self-expanding stent element from a manufactured diameter to an expanded diameter of the graft component. The methods may also include coupling the self-expanding stent element to the graft component at the expanded diameter of the graft component. In addition, the methods may include inducing plastic strain in the self-expanding stent element by reducing the self-expanding endoprosthesis to the reduced configuration.

Various aspects of the present disclosure are also directed toward methods of treating a target location in a vessel of a patient with a self-expanding endoprosthesis having a reduced configuration and a deployed configuration. The methods may include arranging the self-expanding endoprosthesis at the target location. The self-expanding endoprosthesis may include a self-expanding stent element having a manufactured diameter and an expanded diameter and a graft component attached to the self-expanding stent element and having an enlarged diameter less than the enlarged diameter of the self-expanding stent element in the deployed configuration. The graft component may be coupled to the self-expanding stent element to reduce the self-expanding stent element from the manufactured diameter to the expanded diameter of the graft component. The self-expanding stent may be configured to exhibit plastic strain in response to being reduced to the reduced configuration, and to exhibit plastic strain at the deployed diameter. The methods may also include expanding the self-expanding endoprosthesis from the reduced configuration to the deployed configuration.

According to one example ("Example 1"), a self-expanding endoprosthesis having a reduced configuration and a deployed configuration, the self-expanding endoprosthesis including: a self-expanding stent element having an enlarged diameter; and a graft component attached to at least a portion of the self-expanding stent element and having an enlarged diameter less than the enlarged diameter of the self-expanding stent element in the deployed configuration; wherein in the deployed configuration, the self-expanding stent element exerts a radially expansive force to the graft component; the graft component having a yield strength greater than the radially expansive force and being configured to radially maintain the self-expanding stent element at the enlarged diameter of the graft component upon application of a second radially expansive force greater than the radially expansive force of the self-expanding stent element.

According to another example ("Example 2") further to Example 1, the graft component is configured to resist plastic deformation upon application of the second radially expansive force.

According to another example ("Example 3") further to any one of Examples 1-2, the enlarged diameter of the self-expanding stent element is from 2% to 25% greater than the enlarged diameter of the graft component.

According to another example ("Example 4") further to any one of Examples 1-3, the graft component is a continuous structure attached to the self-expanding stent element forming a flow lumen of the self-expanding endoprosthesis.

According to another example ("Example 5") further to any one of Examples 1-4, the self-expanding stent element comprises a plurality of undulations formed by struts connecting apices.

According to another example ("Example 6") further to Example 5, apices comprise intradoses and extradoses, and the graft component is configured to reduce tensile stress in the intradoses of the apices.

According to another example ("Example 7") further to Example 5, apices comprise intradoses and extradoses, and the graft component is configured to maintain compression of the intradoses of the apices.

According to another example ("Example 8") further to Example 7, the self-expanding stent element and the graft component are reduced to a reduced configuration, and the intradoses of the apices remain in compression after expansion to the deployed configuration.

According to another example ("Example 9") further to any one of Examples 1-8, the self-expanding stent element is heat set to a manufactured diameter.

According to another example ("Example 10") further to Example 9, the manufactured diameter of the self-expanding stent element is from 15% to 20% greater than the enlarged diameter of the graft component.

According to another example ("Example 11") further to any one of Examples 1-10, the manufactured diameter of the self-expanding stent element is from approximately 1 mm to 3 mm greater than the enlarged diameter of the graft component.

According to another example ("Example 12") further to any one of Examples 1-11, the self-expanding stent element and the graft component are configured to compress to a reduced diameter from 4 French to 26 French.

According to another example ("Example 13") further to Example 12, the enlarged diameter of the graft component is from 2 mm to 53 mm.

According to another example ("Example 14") further to any one of Examples 1-3, the self-expanding stent element with a manufactured diameter of from 7 mm to 32 mm and the graft component has an expanded diameter of from 5 mm to 27 mm.

According to another example ("Example 15") further to Example 14, the graft component is configured to resist a radially expansive force greater than an outward force from the self-expanding stent element without expanding beyond the expanded diameter of the graft component, and the radially expansive force is between 3 atm and 6 atmosphere atm.

According to one example ("Example 16"), a self-expanding endoprosthesis includes: a self-expanding stent element with a manufactured diameter of from 7 mm to 32 mm; a graft component with an expanded diameter of from 5 mm to 27 mm; wherein a self-deployed diameter of the self-expanding stent element is at least from 2% to 25% greater than the expanded diameter of the graft component; wherein the self-expanding stent element is attached at least in part to the graft component; wherein when the self-expanding endoprosthesis is fully deployed, the self-expanding stent element continues to apply outward force against the graft component without expanding beyond the expanded diameter of the graft component.

According to another example ("Example 17") further to Example 16, the graft component is configured to resist a radially expansive force greater than an outward force from the self-expanding stent element without expanding beyond the expanded diameter of the graft component, and the radially expansive force is between 3 atm and 6 atmosphere atm.

According to another example ("Example 18") further to any one of Examples 16-17, the self-expanding stent element comprises a plurality of undulations formed by struts, the apices comprise intradoses and extradoses, and the graft component is configured to maintain compression of the intradoses of the apices.

According to another example ("Example 19") further to Example 18, the self-expanding stent element is reduced from a manufactured diameter to the self-deployed diameter prior to attachment of the graft component thereto, and attachment arranges the intradoses of the apices in compression.

According to one example ("Example 20"), a self-expanding endoprosthesis including: a self-expanding stent element having a neutral diameter of from 22 mm to 58 mm; a graft component with an expanded diameter of from 20 mm to 53 mm and attached to the self-expanding stent element; wherein the self-expanding stent element and the graft component are configured to reduce to a delivery configuration from a fully-deployed configuration for introduction into a patient; and wherein a self-deployed diameter of the self-expanding stent element is at least from 2% to 25% greater than the expanded diameter of the graft component and the graft component is configured to maintain the self-expanding stent element at the expanded diameter of the graft component.

According to another example ("Example 21") further to Example 20, the self-expanding stent element is oversized relative to the graft component in the fully-deployed configuration to apply an outward force to the graft component.

According to another example ("Example 22") further to Example 20, the graft component is configured to resist a radially expansive force greater than an outward force from the self-expanding stent element without expanding beyond the expanded diameter of the graft component, and the radially expansive force is between 3 atm and 6 atmosphere atm.

According to one example ("Example 23"), a self-expanding endoprosthesis having a reduced configuration and a deployed configuration, the self-expanding endoprosthesis including: a self-expanding stent element having an enlarged diameter; and a diametric constraint coupled to at least a portion of the self-expanding stent element configured to constrain the portion of the self-expanding stent to an enlarged diameter less than the enlarged diameter of the self-expanding stent element in the deployed configuration; wherein in the deployed configuration, the self-expanding stent element exerts a radially expansive force to the graft component; the graft component having a yield strength greater than the radially expansive force and being configured to radially maintain the self-expanding stent element at the enlarged diameter of the graft component upon application of a second radially expansive force greater than the radially expansive force of the self-expanding stent element.

According to another example ("Example 24") further to Example 23, the diametric constraint is a filament woven through portions of the self-expanding stent element.

According to one example ("Example 25"), a self-expanding endoprosthesis having a reduced configuration and a deployed configuration, the self-expanding endoprosthesis including: a self-expanding stent element having a manufactured diameter and an expanded diameter; and a graft component attached to the self-expanding stent element and having an enlarged diameter less than the enlarged diameter of the self-expanding stent element in the deployed configuration; wherein the self-expanding stent is configured to exhibit plastic strain in response to being reduced to the reduced configuration and at the deployed diameter.

According to one example ("Example 26"), a method of manufacturing a self-expanding endoprosthesis having a reduced configuration and a deployed configuration, the method including: reducing a self-expanding stent element from a manufactured diameter to an expanded diameter of the graft component; coupling the self-expanding stent element to the graft component at the expanded diameter of the graft component; and inducing plastic strain in the self-expanding stent element by reducing the self-expanding endoprosthesis to the reduced configuration.

According to one example ("Example 27"), a method of treating a target location in a vessel of a patient with a self-expanding endoprosthesis having a reduced configuration and a deployed configuration, the method including: arranging the self-expanding endoprosthesis at the target location, the self-expanding endoprosthesis including a self-expanding stent element having a manufactured diameter and an expanded diameter, a graft component attached to the self-expanding stent element and having an enlarged diameter less than the enlarged diameter of the self-expanding stent element in the deployed configuration, and wherein the graft component is coupled to the self-expanding stent element to reduce the self-expanding stent element from the manufactured diameter to the expanded diameter of the graft component and the self-expanding stent is configured to exhibit plastic strain in response to being reduced to the reduced configuration and at the deployed diameter; and expanding the self-expanding endoprosthesis from the reduced configuration to the deployed configuration.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
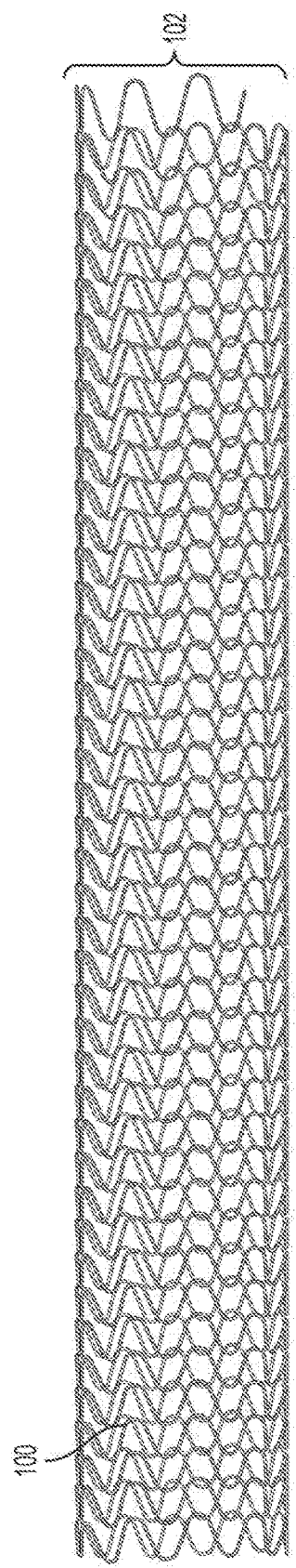
FIG. 1A shows an example self-expanding stent element at a manufactured diameter consistent with various aspects of the present disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosed subject matter as characterized by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Various aspects of the present disclosure are directed toward medical devices (or self-expanding endoprostheses) that include a self-expanding stent element attached to a graft component. In certain instances, the stent-grafts may be delivered to a target location via a transcatheter approach. Thus, the stent-grafts may be reduced to a delivery configuration. Minimizing the delivery profile (e.g., diameter of the stent-grafts in the delivery configuration) may facilitate access to a treatment site and reduce the risk of access site complications.

FIG. 1A shows an example self-expanding stent 100 at a manufactured diameter 102 consistent with various aspects of the present disclosure. The self-expanding stent element 100 is shown in FIG. 1A at the manufactured diameter 102 of the self-expanding stent element 100. In certain instances, the self-expanding stent element 100 may be heat-set at the manufactured diameter 102 of the self-expanding stent element 100. In addition, the self-expanding stent 100 may be a wire-wound stent having a plurality of apices (e.g., as discussed in further detail with reference to FIG. 4). The self-expanding stent 100 may form a portion of a self-expanding endoprosthesis 104 as is shown in FIG. 1B.

Figure 1B:
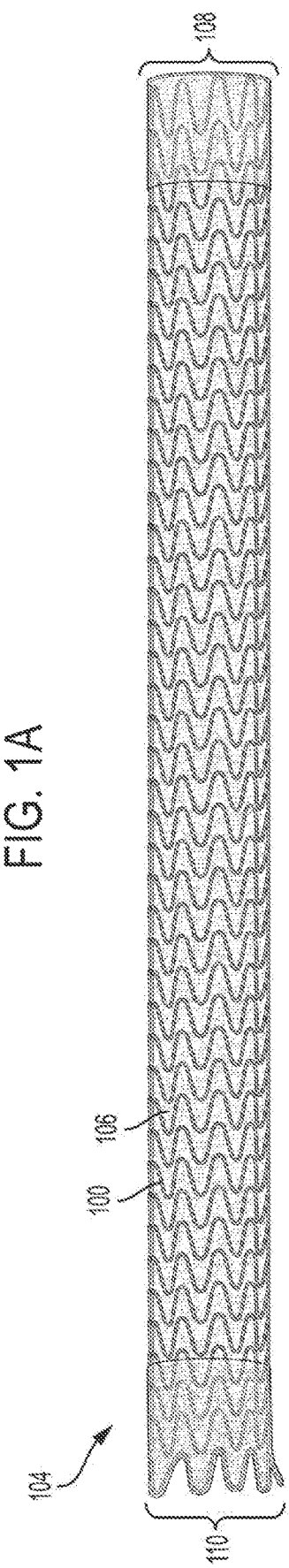
FIG. 1B shows a self-expanding endoprosthesis including a graft component attached to the self-expanding stent element, as shown in FIG. 1A, consistent with various aspects of the present disclosure.

FIG. 1B shows the self-expanding endoprosthesis 104 including a graft component 106 attached to at least a portion of the self-expanding stent element 100. In certain instances, the graft component 106 is a continuous structure attached to the self-expanding stent element 100 forming a flow lumen of the self-expanding endoprosthesis 104. As shown in FIG. 1B, the self-expanding endoprosthesis 104 is shown in a deployed configuration. The graft component 106 is arranged at an expanded diameter 108 of the graft component 106 in the deployed configuration of the self-expanding endoprosthesis 104. In certain instances, the expanded diameter 108 of the graft component 106 in the deployed configuration of the self-expanding endoprosthesis 104 may be from approximately 5 mm to 27 mm.

The manufactured diameter 102 of the self-expanding stent element 100 may be from approximately 1 mm to 5 mm greater than the expanded diameter 108 of the graft component 106 in the deployed configuration of the self-expanding endoprosthesis 104 (e.g., from 2 mm to 5 mm, 5 mm to 13 mm, 35 mm to 53 mm, or any dimension therebetween). In other instances, the manufactured diameter 102 of the self-expanding stent element 100 may be from 2% to 20% greater than the expanded diameter 108 of the graft component 106 in the deployed configuration of the self-expanding endoprosthesis 104. The expanded diameter of the graft component 106 may be less than the expanded diameter 110 of the self-expanding stent element 100. For example, the expanded diameter 108 of the graft component 106 may be from 5 mm to 27 mm, and in other instances, the expanded diameter 108 of the graft component 106 may be from 20 mm to 53 mm. In either instance, the manufactured diameter 102 of the self-expanding stent element 100 is from 2% to 20% greater than the expanded diameter 108 of the graft component 106.

In certain instances, when the self-expanding endoprosthesis 104 is in the deployed configuration, the self-expanding stent element 100 may be configured to exert a radially expansive force along the graft component 106. The graft component 106 may have a yield strength greater than the radially expansive force exerted by the self-expanding stent element 100. In addition, the graft component 106 may be configured to radially maintain the self-expanding stent element 100 at the expanded diameter of the graft component 106 upon application of a second radially expansive force greater than the radially expansive force of the self-expanding stent element 100.

The second radially expansive force may be sufficient to enlarge the graft component 106 to the enlarged diameter without plastic deformation to a diameter larger than the enlarged diameter. The second radially expansive force may depend on the diameter of the self-expanding stent element 100 and/or the graft component 106. For example, a larger diameter graft component 106 may be less resistant to expansive forces than a smaller diameter graft component 106. In certain instances, the second radially expansive force is between 3 atmosphere (atm) and 6 atmosphere (atm). In certain instances, the graft component 106 may have a yield strength such that the second radially expansive force may be applied for 10 seconds, 20 seconds, or 30 seconds without graft component 106 enlarging in diameter by more than 0.5 mm. In certain instances, the graft component 106 does not enlarge more than 0.1 mm, 0.2 mm, or 0.3 mm, or 0.4 mm in response to a force applied thereto.

In certain instances, the graft component 106 is configured to resist plastic deformation (and/or resist fracture and breaking) upon application of the second radially expansive force. The graft component 106, for example, may be configured to maintain the self-expanding endoprosthesis 104 at the expanded diameter 108 of the graft component 106 in response to the second radially expansive force. The graft component 106 mitigates against expansion of the self-expanding endoprosthesis 104 as opposed to allowing the self-expanding endoprosthesis 104 to expand in response to the second radially expansive force.

In addition, the manufactured diameter 102 of the self-expanding stent element 100 may be from 7 mm to 32 mm with the expanded diameter 108 of the graft component 106 being from 5 mm to 27 mm. In certain instances, the manufactured diameter 102 of the self-expanding stent element 100 may be from 22 mm to 58 mm with the expanded diameter 108 of the graft component 106 being from 20 mm to 53 mm (1 mm to 5 mm less than the manufactured diameter 102 of the self-expanding stent element 100). In certain instances, the expanded diameter 110 of the self-expanding stent element 100 is from 2% to 25% greater than the expanded diameter 108 of the graft component 106 after plastic deformation from the manufactured diameter 102.

Figure 1C:
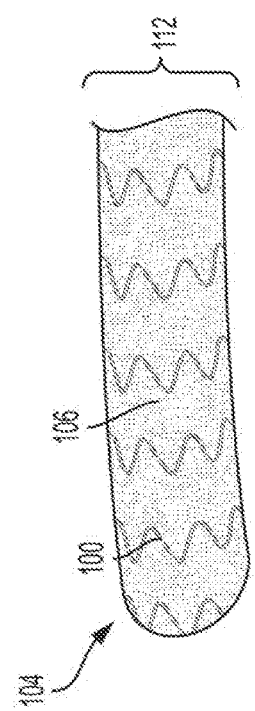
FIG. 1C shows the self-expanding endoprosthesis, as shown in FIG. 1B, at a reduced diameter thereof consistent with various aspects of the present disclosure.

FIG. 1C shows the self-expanding endoprosthesis 104, as shown in FIG. 1A, at a reduced diameter 112 thereof consistent with various aspects of the present disclosure. At the reduced diameter 112, the self-expanding endoprosthesis 104 may be configured at a delivery configuration for insertion into a patient. In addition, the self-expanding stent element 100 and the graft component 106 are configured to reduce to the reduced diameter 112 between approximately 4 French to approximately 24 French. Other reduced diameters are possible, depending on diameter of the self-expanding stent element 100 and the graft component 106. In certain instances, the self-expanding endoprosthesis 104 is reduced to a diameter such that the self-expanding stent element 100 incurs plastic strain.

In certain instances, the self-expanding endoprosthesis 104 may be reduced in size beyond plastic strain initiation in the self-expanding stent element 100, for example, the self-expanding endoprosthesis 104 may be reduced to 0.5 mm, 1 mm, 1.5 mm, 2 mm, 2.5 mm, 3 mm, 3.5 mm, 4 mm, 4.5 mm, or 5 mm (depending on a diameter of the self-expanding endoprosthesis 104) beyond plastic strain initiation of the self-expanding stent element 100. The self-expanding stent element 100 of the self-expanding endoprosthesis 104 may be configured to maintain plastic strain after deployment from the delivery configuration, shown in FIG. 1C, to the deployed configuration shown in FIG. 1B. The self-expanding endoprosthesis 104 may be delivered from the delivery (or reduced) configuration to the deployed configuration at a target location within a patient's vasculature for treatment thereof.

The manufactured diameter 102 of the self-expanding stent element 100 may be considered the diameter to which the self-expanding stent element 100 would deploy if plastic strain has not been induced, and if it were not coupled to the graft component 106. The self-expanding stent element 100 may be reduced from the manufactured diameter 102 of the self-expanding stent element 100 to couple the graft component 106 thereto. The manufactured diameter 102 of the self-expanding stent element 100 may be considered may be considered a neutral, nominal, self-deployed, or unbiased diameter. For example, the neutral or nominal diameter 102 of the self-expanding stent element 100 may be neutral or nominal such that the self-expanding stent element 100 would recover to the neutral or nominal diameter 102 if the self-expanding stent element 100 were not plastically deformed.

In certain instances, thermally setting all or part the self-expanding stent element 100 to a diameter greater than the expanded diameter 108 of the graft component 106 may pre-strain the self-expanding stent element 100. Pre-strain of the self-expanding stent element 100 may negate or offset the effect of plastic deformation occurring in the crush/load process, which reduces the self-expanding endoprosthesis 104 from the deployed configuration, shown in FIG. 1B, to the delivery configuration shown in FIG. 1C.

The illustrative components shown in FIG. 1 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 1 may be, in embodiments, integrated with various other components depicted therein (and/or components not illustrated), all of which are considered to be within the ambit of the disclosed subject matter.

Figure 2A:
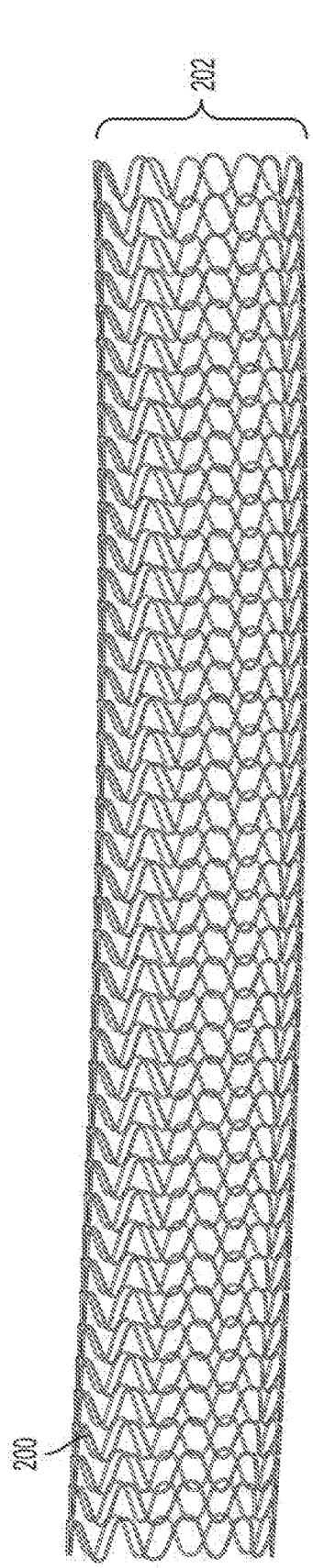
FIG. 2A shows another example self-expanding stent at an expanded diameter consistent with various aspects of the present disclosure.

FIG. 2A shows another example self-expanding stent 200 at a manufactured diameter 202 consistent with various aspects of the present disclosure. The manufactured diameter 202 of the self-expanding stent 200 may be from 2 mm to 13 mm or from 35-53 mm or anywhere between. In certain instances, the self-expanding stent 200 may be heat-set at the manufactured diameter 202 of the self-expanding stent 200. In addition, the self-expanding stent 200 may be a wire-wound stent having a plurality of apices (e.g., as discussed in further detail with reference to FIG. 4). In addition, the self-expanding stent 200 may form a portion of an implantable stent-graft device 204 as is shown in FIG. 2B.

Figure 2B:
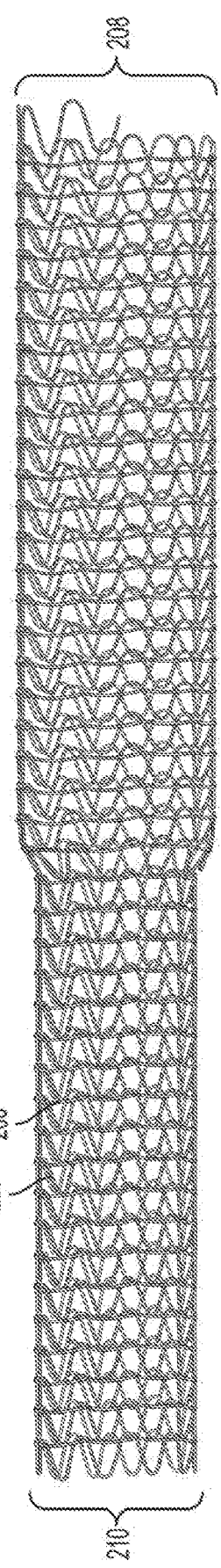
FIG. 2B shows a first configuration of a diametric constraint and the self-expanding stent element, as shown in FIG. 2A, consistent with various aspects of the present disclosure.

FIG. 2B shows a first configuration of a diametric constraint 206 and the self-expanding stent element 200, as shown in FIG. 2A, at a first expanded diameter 208 and a second expanded diameter 210 of the diametric constraint 206 consistent with various aspects of the present disclosure. As shown in FIG. 2B, the diametric constraint 206 is a filament woven through portions of the self-expanding stent element 200. The filament may be a material similar to the continuous graft component. In other instances, the diametric constraint 206 may be a continuous graft component (e.g., as shown in FIG. 1B) as opposed to a wire structure. In either instance, the diametric constraint 206 may be arranged such that the implantable stent-graft device 204 includes more than one diameter. In certain instances, either of the first expanded diameter 208 and the second expanded diameter 210 of the diametric constraint 206 includes an expanded diameter from 5 mm to 27 mm. More specifically, the manufactured diameter 202 of the self-expanding stent 200 may be approximately 1 mm to 5 mm greater than either of the first expanded diameter 208 and the second expanded diameter 210 of the diametric constraint 206.

In certain instances, the self-expanding stent element 200 may have a self-deployed diameter that is at least from 2% to 25% greater than the first expanded diameter 208 and the second expanded diameter 210 of the diametric constraint 206 is when the diametric constraint 206 is attached thereto. The self-deployed diameter of the self-expanding stent element 200 may be considered the diameter to which the self-expanding stent element 200 would deploy if it were not coupled to the diametric constraint 206. The self-expanding stent element 200 may be reduced from the manufactured diameter 202 of the self-expanding stent 200 to couple the diametric constraint 206 thereto. In addition and as noted above with reference to FIG. 1C, the implantable stent-graft device 204 may be reduced to a delivery configuration for implantation into a patient. In certain instances, reducing the implantable stent-graft device 204 to the delivery configuration and/or reducing the self-expanding stent element 200 from the manufactured diameter 202 may plastically deform the self-expanding stent element 200 such that the self-expanding stent element 200 may be configured to deploy to the self-deployed diameter that is at least the first expanded diameter 208 and the second expanded diameter 210 of the diametric constraint 206.

In addition, the self-expanding stent element 200 may be configured, when the implantable stent-graft device 204 is fully-deployed (as shown in FIG. 2B), the self-expanding stent element 200 may be configured to continue to apply outward force against the diametric constraint 206 without expanding beyond the first expanded diameter 208 and the second expanded diameter 210 of the diametric constraint 206. Further, in certain instances, the diametric constraint 206 may be configured to resist a radially expansive force greater than the outward force from the self-expanding stent element 200 without expanding beyond the first expanded diameter 208 and the second expanded diameter 210. The radially expansive force may depend on the diameter of the self-expanding stent element 200 and/or the diametric constraint 206. For example, a larger diameter diametric constraint 206 may be less resistant to expansive forces than a smaller diameter diametric constraint 206. In certain instances, the radially expansive force being between 3 atm and 6 atm.

Figure 2C:
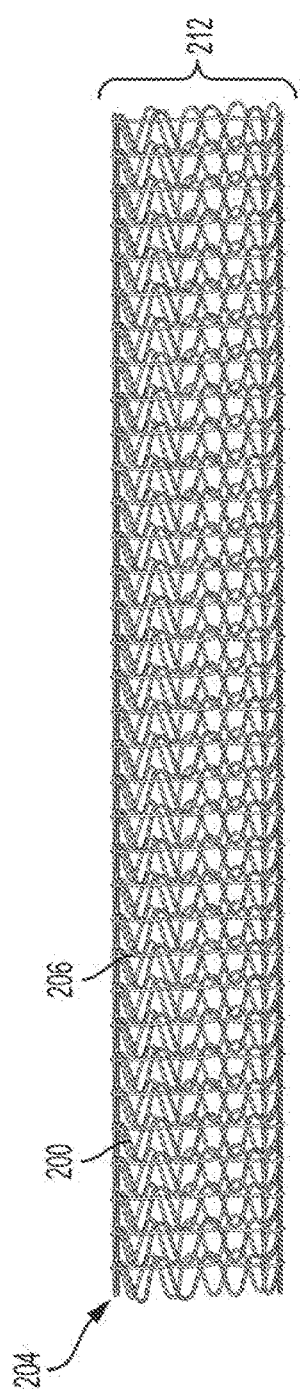
FIG. 2C shows a second configuration of the diametric constraint and the self-expanding stent element, as shown in FIG. 2A, consistent with various aspects of the present disclosure.

FIG. 2C shows a second configuration of the diametric constraint 206 attached to the self-expanding stent element 200, as shown in FIG. 2A. As shown in FIG. 2C, the diametric constraint 206 is a wire structure woven through portions of the self-expanding stent element 200. In other instances, the diametric constraint 206 may be a continuous graft component (e.g., as shown in FIG. 1B) as opposed to a wire structure. The diametric constraint 206 may be attached to the self-expanding stent element 200 such that the diametric constraint 206 includes a single expanded diameter 212.

Figure 3:
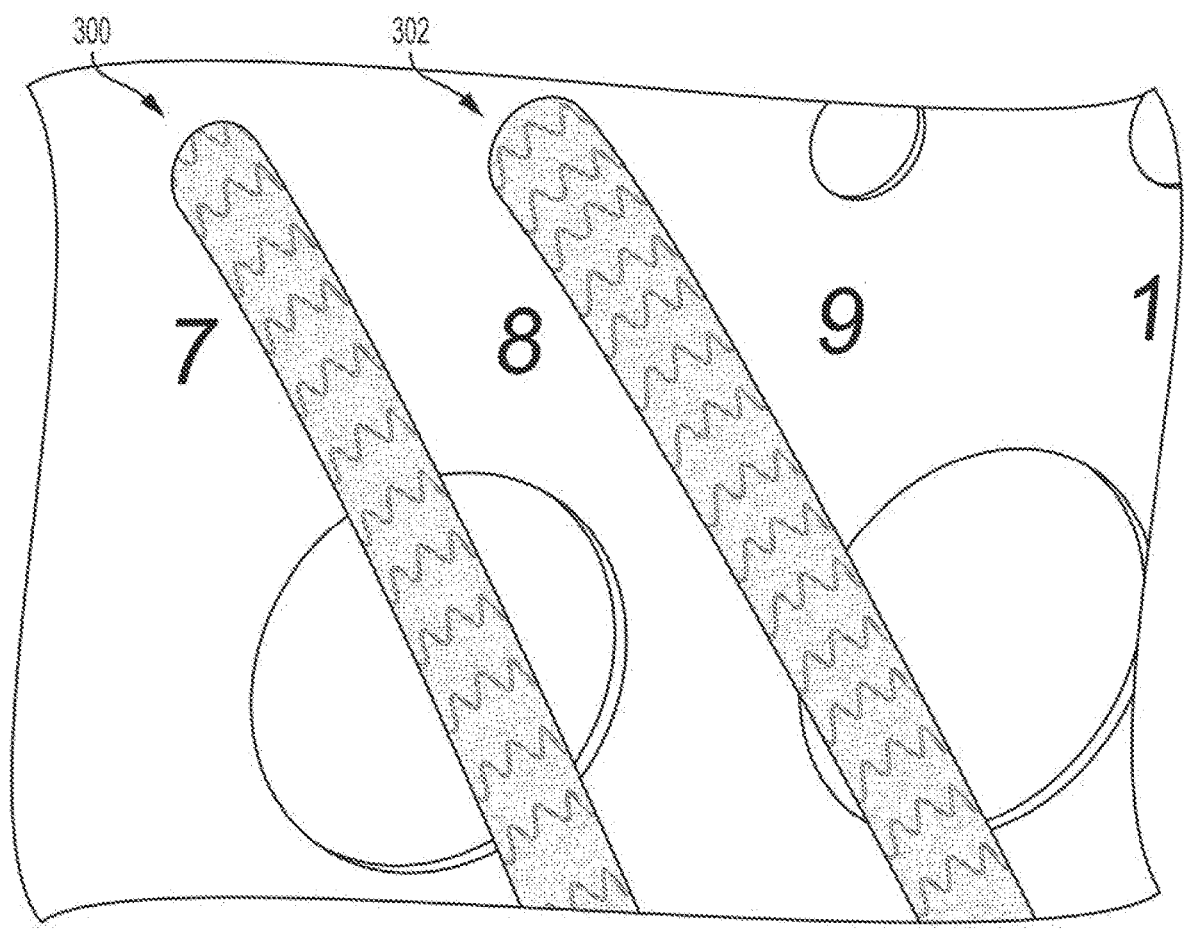
FIG. 3 shows an example self-expanding endoprosthesis in reduced configurations consistent with various aspects of the present disclosure.

FIG. 3 shows example self-expanding endoprosthesis 300, 302 in reduced configurations consistent with various aspects of the present disclosure. The self-expanding endoprostheses 300, 302 each include a graft component and a pre-strained stent component. The pre-strained stent component of the self-expanding endoprostheses 300, 302 may include reduced wire diameters to allow for the low profile reduced (delivery) configuration shown. The wire diameter of a stent of an endoprosthesis may contribute to a structural strength thereof. The forces may be applied in reducing an endoprosthesis to a reduced (delivery) configuration and forces acting on the endoprosthesis when implanted into the body may limit the size of the wire diameter. Pre-straining the stent component of the self-expanding endoprosthesis 300, 302 may enhance the ability of the stent component to withstand radial forces applied to the self-expanding endoprosthesis 300, 302. In addition, the reduced wire diameters of the pre-strained stent component of the self-expanding endoprosthesis 300, 302 optimizes reduced (delivery) configuration allowing for the self-expanding endoprosthesis 300, 302 to reduce to a smaller reduced (delivery) configuration as compared to an equally sized device not having pre-strained stent component if the wire diameters are equal.

As discussed in further detail below with reference to FIG. 6, a pre-strained stent component may also optimize deployed diameter, radial force and fatigue life and decrease stiffness due to the reduced wire diameter. Further the pre-strained stent component may also increase compression resistance (radial) due to the pre-strained condition and/or the pre-strained stent component having a manufactured (or relaxed) stent diameter greater than the expanded diameter after graft component attachment.

Figure 4:
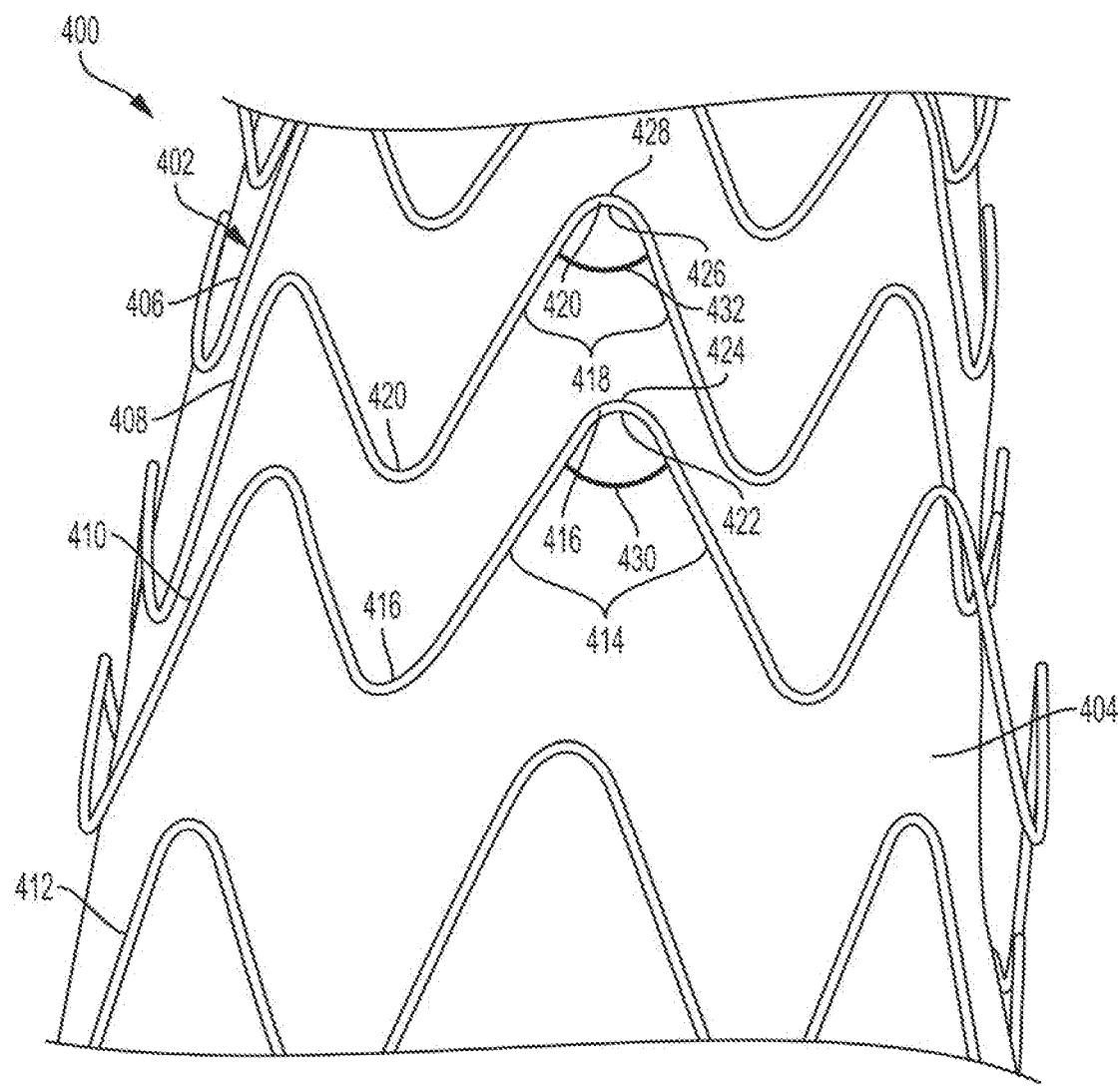
FIG. 4 shows another example self-expanding endoprosthesis consistent with various aspects of the present disclosure.

FIG. 4 shows another example implantable stent-graft device 400 consistent with various aspects of the present disclosure. The self-expanding implantable stent-graft device 400 includes a self-expanding stent element 402 and a graft component 404. As shown in FIG. 4, the self-expanding stent element expands beyond the diameter of the graft component 404 if the self-expanding stent element is not constrained by the graft component 404.

The self-expanding stent element 402 may have a manufactured diameter of from 7 mm to 32 mm with the graft component 404 having an expanded diameter of from 5 mm to 27 mm. In certain instances, the self-expanding stent element 402 may have a manufactured diameter of 22 mm to 58 mm with the graft component 404 having an expanded diameter of 20 mm to 53 mm or 1 mm to 5 mm less than the manufactured diameter of the self-expanding stent element 402. More specifically, the manufactured diameter of the self-expanding stent element 402 may be approximately 1 mm to 3 mm greater than the expanded diameter of the graft component 404. In addition, the self-expanding stent element 402 includes a self-deployed diameter (e.g., if the self-expanding stent element 402 were not attached to the graft component 404) that is from 2% to 25% greater than the expanded diameter of the graft component 404. When the implantable stent-graft device 400 is fully deployed, the self-expanding stent element 402 may be configured to apply outward force against the graft component 404 without expanding the graft component 404 beyond the expanded diameter thereof. Further, in certain instances, the graft component 404 may be configured to resist a radially expansive force greater than the outward force from the self-expanding stent element 402 without expanding beyond the expanded diameter of the graft component 404. The radially expansive force may depend on the diameter of the self-expanding stent element 402 and/or the graft component 404. For example, a larger diameter graft component 404 may be less resistant to expansive forces than a smaller diameter graft component 404 with the radially expansive force being between 3 atm and 6 atm.

The self-expanding stent element 402 may include a plurality of undulations. As shown in FIG. 4, the self-expanding stent element 402 includes multiple rows 406, 408, 410, 412 which forming the plurality of undulations. Although highlighted on two sets of the undulations, each of the plurality of undulations is formed by struts 414, 418 interconnected at apices 416, 420. The apices 416, 420 includes intradoses 422, 426 (internal portion of an apex) and extradoses 424, 428 (external portion of an apex).

In certain instances, the graft component 404 may be attached to the self-expanding stent element 402 and configured to reduce tensile stress in the intradoses 422, 426 of the apices 416, 420 In certain instances, reducing the implantable stent-graft device 400 to the delivery configuration and/or reducing the self-expanding stent element 402 from the manufactured diameter to attach the graft component 404 thereto may plastically deform the self-expanding stent element 402 such that the intradoses 422, 426 of the apices 416, 420 are arranged in compression. After plastic deformation of the self-expanding stent element 402, deploying the self-expanding stent element 402 and the graft component 404 to a fully deployed configuration, tensile stress within the intradoses 422, 426 of the apices 416, 420 are reduced because the self-expanding stent element 402 is maintained in configuration less than the manufactured diameter. Intradoses 422, 426 in tension may be more likely to fracture or break than intradoses 422, 426 not in tension or in compression. Thus, reducing tension within the intradoses 422, 426 of the apices 416 may improve fatigue resistance and reliability of the self-expanding stent element 402.

In addition, the graft component 404 may be attached to the self-expanding stent element 402 and configured to maintain compression of the intradoses 422, 426 of the apices 416, 420. In certain instances, reducing tensile stress may occur by maintaining the intradoses 422, 426 of the apices 416, 420 in compression. For illustrative purposes, however, row 410 of the plurality of undulations of the self-expanding stent element 402 is shown unattached to the graft component 404. The compression of the attached intrados 426 as compared to an unattached intrados 422 is illustrated by a difference in lengths 430, 432 between the struts 414, 418 as the length 432 between the struts 418 of the attached intrados 426 is less than the length 430 between the struts 414 of the unattached intrados 422 due to the attached intrados 426 being in compression.

In certain instances, the graft component 404 configured to maintain compression of the intradoses 422, 426 of the apices 416, 420 in a fully-deployed (expanded) configuration. In addition, the graft component 404 configured to maintain compression of the intradoses 422, 426 in response to the radially expansive force greater than the outward force from the self-expanding stent element without expanding beyond the expanded diameter of the graft component 404. In addition, the self-expanding stent element 402 may be reduced from the manufactured diameter to couple the graft component 404 thereto. In addition and as noted above with reference to FIG. 1C and FIG. 3, the implantable stent-graft device 400 may be reduced to a delivery configuration for implantation into a patient. As noted above, reducing the implantable stent-graft device 400 may plastically deform the self-expanding stent element 402 such the intradoses 422, 426 of the apices 416, 420 are arranged in compression.

The manufactured diameter of the self-expanding stent element 402 may be considered may be considered a neutral, nominal, self-deployed diameter, or unbiased diameter. For example, the neutral or nominal diameter of the self-expanding stent element 402 may be neutral or nominal such that the self-expanding stent element 402 would recover to the neutral or nominal diameter if the self-expanding stent element 402 were not plastically deformed.

Maintaining the intradoses 422, 426 of the apices 416, 420 in compression may mitigate against failure of the self-expanding stent element 402. Tension in the intradoses 422, 426 of the apices 416, 420 may cause the intradoses 422, 426 to crack, which may negatively impact fatigue life of the self-expanding stent element 402. In addition, maintaining the intradoses 422, 426 of the apices 416, 420 in compression may facilitate uniform expansion of the self-expanding device 400 from the delivery configuration to the fully-deployed (expanded) configuration. In addition, crushing or reducing the self-expanding device 400 to the delivery configuration may plastically deform the self-expanding stent element 402 affiliating the ability of the graft component 404 to maintain the intradoses 422, 426 of the apices 416, 420 in compression.

Figure 5:
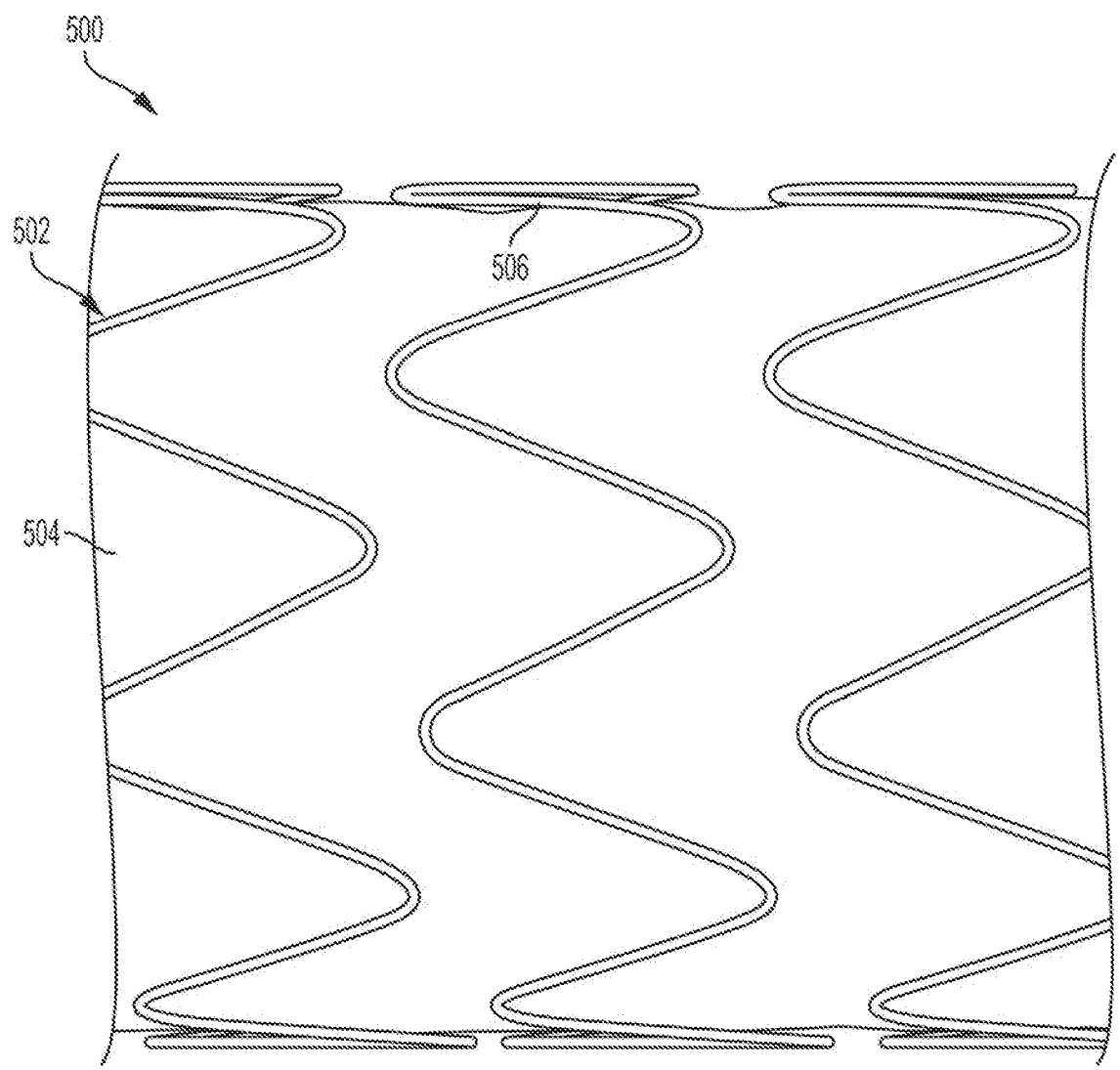
FIG. 5 shows an example self-expanding endoprosthesis including a graft component and a self-expanding stent element with portions of the self-expanding stent element unattached from the graft component consistent with various aspects of the present disclosure.

FIG. 5 shows an example self-expanding endoprosthesis 500 including a graft component 504 and a self-expanding stent element 502 with portions 506 of the self-expanding stent element 502 unattached from the graft component 504 consistent with various aspects of the present disclosure. Portions of the self-expanding stent element 502 are shown unattached from the graft component 504 for illustrative purposes. All aspects of the self-expanding stent element 502 may be attached to the graft component 504.

Portions of the self-expanding stent element 502 are shown unattached from the graft component 504. The expanding stent element 502 may include a self-deployed diameter (e.g., if the self-expanding stent element 502 were not attached to the graft component 504) that is from 2% to 25% greater than an expanded diameter of the graft component 504. The self-expanding stent element 502 may have a manufactured diameter of from 5 mm to 27 mm (or 5 mm-53 mm) with the graft component 504 having an expanded diameter of from 5 mm to 27 mm or where self-expanding stent element 502 has a diameter of 1 mm to 5 mm (2%-25%) greater than graft component 504. In certain instances, the self-expanding stent element 502 may have a manufactured diameter of 22 mm to 58 mm with the graft component 504 having an expanded diameter of 20 mm to 53 mm or 1 mm to 5 mm less than the manufactured diameter of the self-expanding stent element 502. More specifically, the manufactured diameter of the self-expanding stent element 502 may be greater than the expanded diameter of the graft component 504. In addition and in certain instances, the self-expanding stent element 502 may be oversized relative to the graft component 504 in the fully-deployed configuration to apply an outward force to the one graft component 504.

In addition, the self-expanding stent element 502 may be reduced down from the manufactured diameter to the expanded diameter of the graft component 504 for attachment thereto. Due to reducing the self-expanding stent element 502 or due to reducing the self-expanding stent element 502 to a delivery configuration (e.g., as shown in FIG. 1C and FIG. 3), the self-expanding stent element 502 is configured to deploy to the self-deployed diameter, but is held to the expanded diameter of the graft component 504 by attachment thereto.

When the implantable stent-graft device 500 is fully deployed, the self-expanding stent element 502 may be configured to apply outward force against the graft component 504 without expanding the graft component 504 beyond the expanded diameter thereof. Further, in certain instances, the graft component 504 may be configured to resist a radially expansive force greater than the outward force from the self-expanding stent element 502 without expanding beyond the expanded diameter of the graft component 504 (e.g., manufactured diameter of the graft component 504). The radially expansive force may depend on the diameter of the self-expanding stent element 502 and/or the graft component 504. For example, a larger diameter graft component 504 may be less resistant to expansive forces than a smaller diameter graft component 504 with the radially expansive force being between 3 atm and 6 atm. For example, in certain instances, with the radially expansive force being between 3 atm and 6 atm for a time period of 1, 2, 5, 10, 20 or 30 seconds without increasing diameter of the implantable stent-graft device 500 greater than approximately 0.5 mm.

The manufactured diameter of the self-expanding stent element 502 may be considered may be considered a neutral, nominal, self-deployed diameter, or unbiased diameter. As noted above, the self-expanding stent element 502 may be plastically deformed by reducing the self-expanding stent element 502 from the manufactured or nominal diameter. For example, the neutral or nominal diameter of the self-expanding stent element 502 may be neutral or nominal such that the self-expanding stent element 502 would recover to the neutral or nominal diameter if the self-expanding stent element 502 were not plastically deformed.

The illustrative components shown in FIG. 5 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 5 may be, in embodiments, integrated with various other components depicted therein (and/or components not illustrated), all of which are considered to be within the ambit of the disclosed subject matter. For example, the graft component 504 may be configured to maintain intradoses of apices of the self-expanding stent element 502 in compression as discussed above with reference to FIG. 4.

Figure 6:
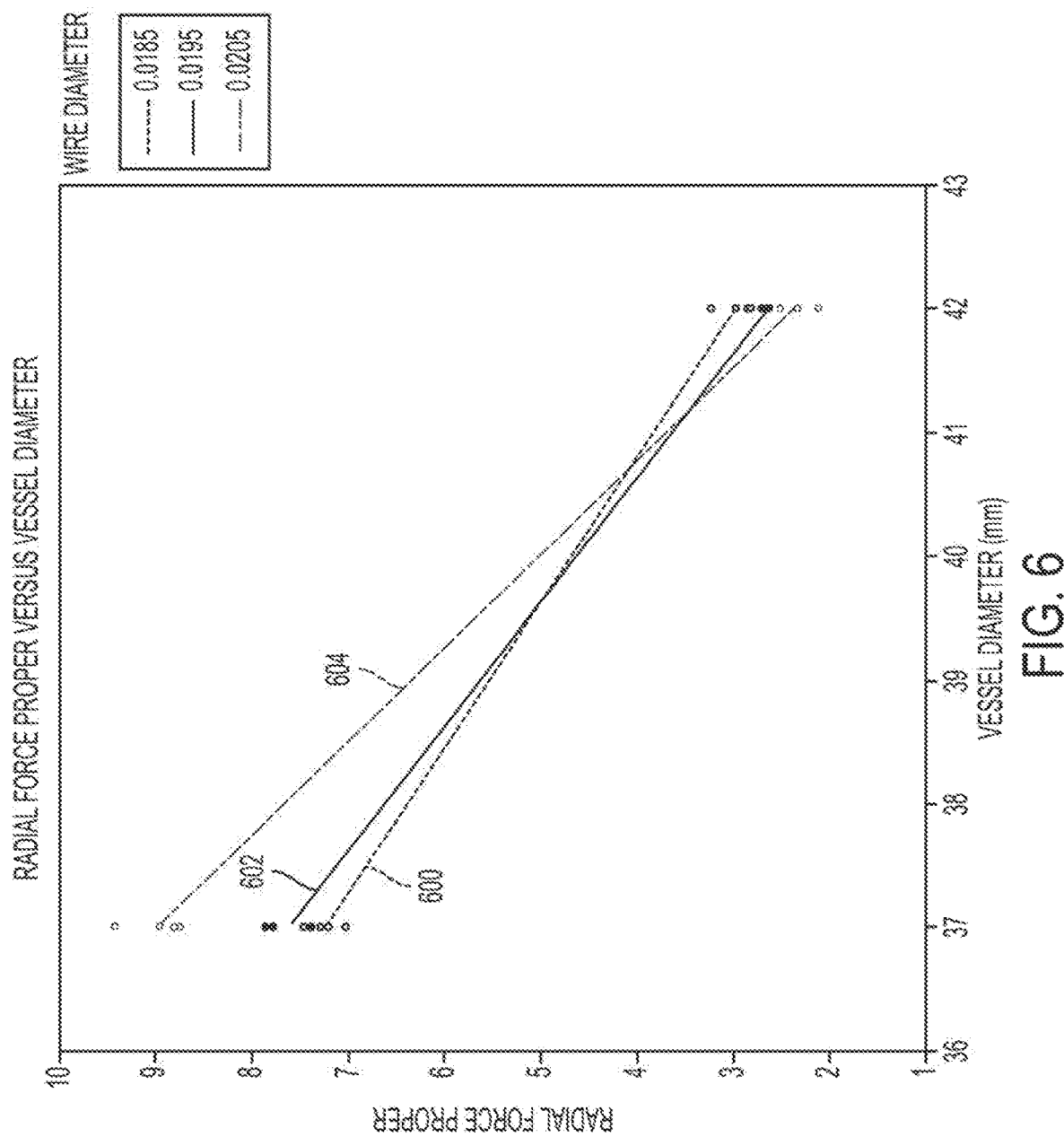
FIG. 6 shows a graph consistent with various aspects of the present disclosure.

FIG. 6 shows a graph consistent with various aspects of the present disclosure. The graph includes plots 600, 602, 604 of endoprosthesis having a graft component and a stent component with the stent component having different diameters. Plot 600 shows radial force applied to an endoprosthesis having a pre-strained stent element with a wire diameter of 0.0185 in. at various endoprosthesis diameters. The pre-strained stent has a manufactured diameter of 4 mm greater than an expanded diameter of the graft component. Plot 602 shows radial force applied to an endoprosthesis having a pre-strained stent element with a wire diameter of 0.0195 in. at various endoprosthesis diameters. The pre-strained stent has a manufactured diameter of 2 mm greater than an expanded diameter of the graft component. Plot 604 shows radial force applied to endoprosthesis having a non-pre-strained stent element with a wire diameter of 0.0205 in. at various endoprosthesis diameters.

The slopes of plots 600, 602 (pre-strained) are less than the slope of plot 604 (not pre-strained). Pre-straining the stent component may enhance the ability of the stent component to withstand radial forces applied to the self-expanding endoprosthesis 300, 302. Thus, the endoprosthesis of plots 600, 602 (pre-strained) may reduce to approximately the same or reduced (delivery) configuration as compared to the endoprosthesis of plot 604 (not pre-strained but with a larger wire diameter). In some cases, the endoprosthesis of plots 600, 602 (pre-strained) may reduce to a smaller delivery configuration.

In addition, the endoprosthesis of plots 600, 602 (pre-strained) may be approximately equally resistant to radial compression at full deployed diameter as the endoprosthesis of plot 604 (not pre-strained) while using a smaller diameter stent wire. Further, pre-strain of the stent frame may increase the material strain and resulting plastic deformation in the stent component 200 at crush/load of the endoprosthesis to the reduced (delivery) configuration. Plastic deformation may result in residual compressive stress at the surface of the stent component (e.g., intradoses 422,426). Additionally, the stent component may not expand beyond the graft diameter after deployment of the endoprosthesis, which may limit the amount of tensile loading imparted on compressively, plastically deformed elements to thereby mitigate associated fatigue failure modes.

The illustrative components shown in FIG. 6 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 6 may be, in embodiments, integrated with various other components depicted therein (and/or components not illustrated), all of which are considered to be within the ambit of the disclosed subject matter.

Figure 7:
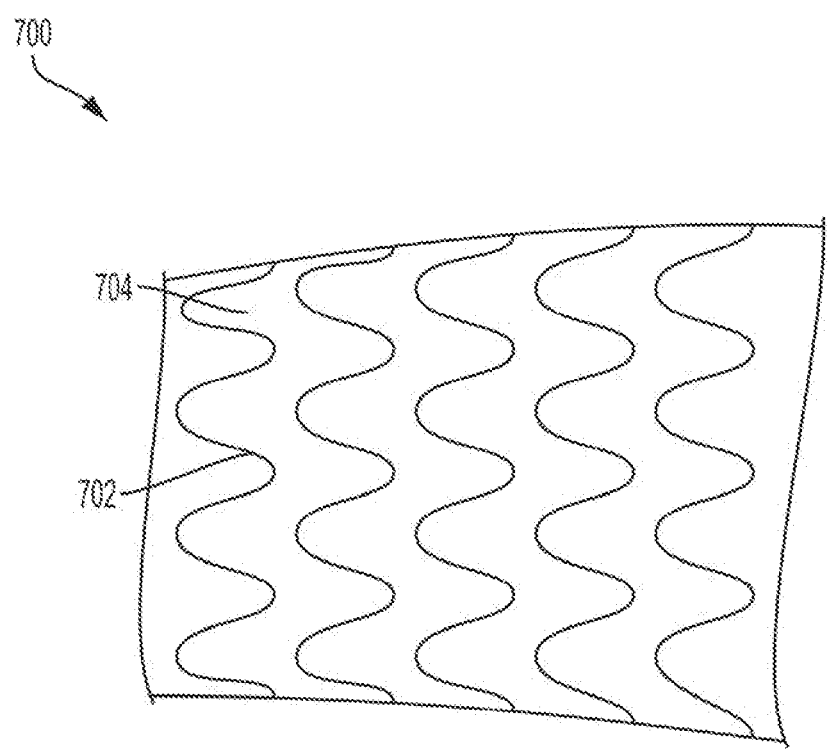
FIG. 7 shows a self-expanding endoprosthesis consistent with various aspects of the present disclosure.

FIG. 7 shows a self-expanding endoprosthesis 700 consistent with various aspects of the present disclosure. The self-expanding endoprosthesis 700 may include a self-expanding stent element 702 and a graft component 704. The self-expanding endoprosthesis 700 may be tapered to such that one end of the self-expanding endoprosthesis 700 has a diameter less than another end of the self-expanding endoprosthesis 700, with the intermediate section decreasing in diameter therebetween.

As discussed in further detail above, the self-expanding stent element 702 may be plastically deformed from a manufactured diameter (greater than the expanded diameter). The self-expanding stent element 702 may be configured to exhibit plastic deformation. The graft component 704 may be attached to the self-expanding stent element 702 such that an expanded diameter (or diameters due to the taper of the self-expanding endoprosthesis 700) of the self-expanding stent element 702 is from 2% to 25% greater than an expanded diameter (or diameters due to the taper of the self-expanding endoprosthesis 700) of the graft component 704 after the self-expanding stent element 702 has been plastically deformed from a manufactured diameter (greater than the expanded diameter).

The illustrative components shown in FIG. 7 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 7 may be, in embodiments, integrated with various other components depicted therein (and/or components not illustrated), all of which are considered to be within the ambit of the disclosed subject matter.

Figure 8:
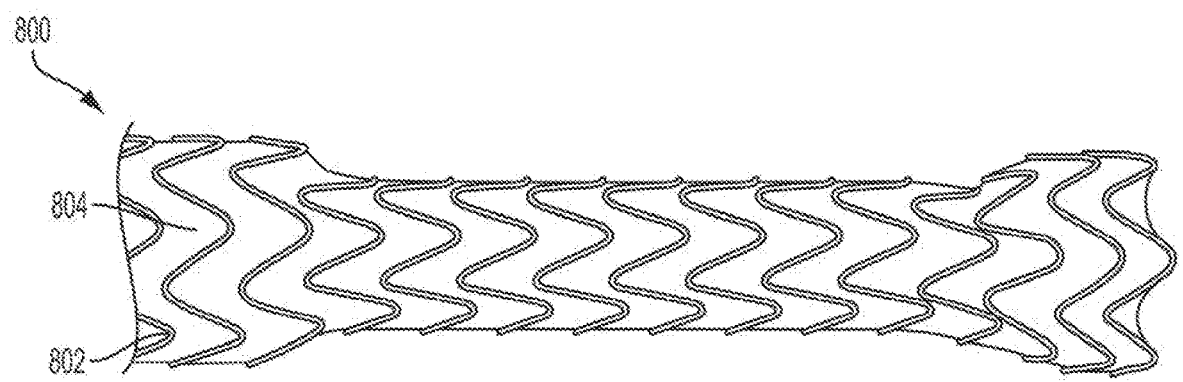
FIG. 8 shows another self-expanding endoprosthesis consistent with various aspects of the present disclosure.

FIG. 8 shows another self-expanding endoprosthesis consistent with various aspects of the present disclosure. The self-expanding endoprosthesis 800 may include a self-expanding stent element 802 and a graft component 804. The self-expanding endoprosthesis 800 may include portions of differing dimensions such that ends of the self-expanding endoprosthesis 800 have a diameter less than an intermediate section therebetween. The self-expanding endoprosthesis 800 may have a dog-bone shape as shown in FIG. 8.

As discussed in further detail above, the self-expanding stent element 802 may be plastically deformed from a manufactured diameter (greater than the expanded diameter). In certain instances, only ends of the self-expanding endoprosthesis 800 may be configured in this manner. In other instances, the entirety of the self-expanding endoprosthesis 800 may be configured with the self-expanding stent element 802 may being plastically deformed. The self-expanding stent element 802 may be configured to exhibit plastic deformation. The graft component 804 may be attached to the self-expanding stent element 802 such that an expanded diameter (or diameters due to the taper of the self-expanding endoprosthesis 800) of the self-expanding stent element 802 is from 2% to 25% greater than an expanded diameter (or diameters due to the taper of the self-expanding endoprosthesis 800) of the graft component 804 after the self-expanding stent element 802 has been plastically deformed from a manufactured diameter (greater than the expanded diameter).

The illustrative components shown in FIG. 8 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 8 may be, in embodiments, integrated with various other components depicted therein (and/or components not illustrated), all of which are considered to be within the ambit of the disclosed subject matter.

The graft components, as discussed herein, may be made up of any material which is suitable for use as a graft in the chosen body lumen and being resistant to expansion beyond a desired dimension as discussed herein. The graft components may be composed of the same or different materials. Furthermore, the graft components may include multiple layers of material that can be the same material or different material. Many graft materials are known, particularly known are those that can be used as vascular graft materials. In one embodiment, said materials can be used in combination and assembled together to comprise a graft. The graft materials used in a stent graft can be extruded, coated or formed from wrapped films, or a combination thereof. Polymers, biodegradable and natural materials can be used for specific applications.

Examples of synthetic polymers include, but are not limited to, nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a graft material. In one embodiment, said graft is made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON®. or GORE-TEX®), and porous or nonporous polyurethanes. In certain instances, the graft comprises expanded fluorocarbon polymers (especially PTFE) materials described in British. Pat. No. 1,355,373; 1,506,432; or 1,506,432 or in U.S. Pat. Nos. 3,953,566; 4,187,390; or 5,276,276, the entirety of which are incorporated by reference. Included in the class of preferred fluoropolymers are polytetrafluoroethylene (PTFE), fluorinated ethylene propylene (FEP), copolymers of tetrafluoroethylene (TFE) and perfluoro(propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is ePTFE. In certain instances, the graft comprises a combination of said materials listed above. In certain instances, the graft is substantially impermeable to bodily fluids. Said substantially impermeable graft can be made from materials that are substantially impermeable to bodily fluids or can be constructed from permeable materials treated or manufactured to be substantially impermeable to bodily fluids (e.g. by layering different types of materials described above or known in the art).

Additional examples of graft materials include, but are not limited to, vinylidinefluoride/hexafluoropropylene hexafluoropropylene (HFP), tetrafluoroethylene (TFE), vinylidenefluoride, 1-hydropentafluoropropylene, perfluoro (methyl vinyl ether), chlorotrifluoroethylene (CTFE), pentafluoropropene, trifluoroethylene, hexafluoroacetone, hexafluoroisobutylene, fluorinated poly(ethylene-co-propylene (FPEP), poly(hexafluoropropene) (PHFP), poly(chlorotrifluoroethylene) (PCTFE), poly(vinylidene fluoride (PVDF), poly(vinylidene fluoride-co-tetrafluoroethylene) (PVDF-TFE), poly(vinylidene fluoride-co-hexafluoropropene) (PVDF-HFP), poly(tetrafluoroethylene-co-hexafluoropropene) (PTFE-HFP), poly(tetrafluoroethylene-co-vinyl alcohol) (PTFE-VAL), poly(tetrafluoroethylene-co-vinyl acetate) (PTFE-VAC), poly(tetrafluoroethylene-co-propene) (PTFEP) poly(hexafluoropropene-co-vinyl alcohol) (PH FP-VAL), poly(ethylene-co-tetrafluoroethylene) (PETFE), poly (ethylene-co-hexafluoropropene) (PEHFP), poly(vinylidene fluoride-co-chlorotrifluoroe-thylene) (PVDF-CTFE), and combinations thereof, and additional polymers and copolymers described in U.S. Publication 2004/0063805, incorporated by reference herein in its entirety for all purposes. Additional polyfluorocopolymers include tetrafluoroethylene (TFE)/perfluoroalkylvinylether (PAVE). PAVE can be perfluoromethylvinylether (PMVE), perfluoroethylvinylether (PEVE), or perfluoropropylvinylether (PPVE), as essentially described in U.S. Publication 2006/0198866 and U.S. Pat. No. 7,049,380, both of which are incorporated by reference herein for all purposes in their entireties. Other polymers and copolymers include, polylactide, polycaprolacton-glycolide, polyorthoesters, polyanhydrides; polyaminoacids; polysaccharides; polyphosphazenes; poly (ether-ester) copolymers, e.g., PEO-PLLA, or blends thereof, polydimethyl-siolxane; poly(ethylene-vingylacetate); acrylate based polymers or copolymers, e.g., poly (hydroxyethyl methylmethacrylate, polyvinyl pyrrolidinone; fluorinated polymers such as polytetrafluoroethylene; cellulose esters and any polymer and copolymers described in U.S. Publication 2004/0063805, incorporated by reference herein in its entirety.

The graft components, as discussed herein, may be attached to the self-expanding stent elements by using a coupling member that is generally a flat ribbon or tape having at least one generally flat surface. In certain instances, the tape member is made from expanded PTFE (ePTFE) coated with an adhesive. The adhesive may be a thermoplastic adhesive. In certain instances, the thermoplastic adhesive may be fluorinated ethylene propylene (FEP). More specifically, an FEP-coated side of the ePTFE may face toward and contacts an exterior surface of the self-expanding stent and graft component, thus attaching the self-expanding stent to the graft component. Materials and method of attaching a stent to the graft is discussed in U.S. Pat. No. 6,042,605 to Martin, incorporated by reference herein for all purposes.

The stent elements discussed herein can be fabricated from a variety of biocompatible materials. These materials may include 316L stainless steel, cobalt-chromium-nickel-molybdenum-iron alloy ("cobalt-chromium"), other cobalt alloys such as L605, tantalum, Nitinol, or other biocompatible metals. In certain instances, as discussed in detail above, the stent (and graft) may be self-expanding. The prosthesis may be balloon expandable The wire wound stent may be constructed from a reasonably high strength material, i.e., one which is resistant to plastic deformation when stressed. In certain instances, the stent comprises a wire which is helically wound around a mandrel having pins arranged thereon so that the helical turns and undulations can be formed simultaneously, as described below. Other constructions also may be used. For example, an appropriate shape may be formed from a flat stock and wound into a cylinder or a length of tubing formed into an appropriate shape or laser cutting a sheet of material. In certain instances, the stent is made from a super-elastic alloy. There are a variety of disclosures in which super-elastic alloys such as nitinol are used in stents. See for example, U.S. Pat. No. 4,503,569, to Dotter; U.S. Pat. No. 4,512,338, to Balko et al.; U.S. Pat. No. 4,990,155, to Wilkoff; U.S. Pat. No. 5,037,427, to Harada, et al.; U.S. Pat. No. 5,147,370, to MacNamara et al.; U.S. Pat. No. 5,211, 658, to Clouse; and U.S. Pat. No. 5,221,261, to Term in et al.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A self-expanding endoprosthesis having a reduced configuration and a deployed configuration, the self-expanding endoprosthesis comprising:
   a self-expanding stent element having an enlarged diameter, the self-expanding stent element configured to exhibit plastic strain at the deployed configuration and in response to being reduced to the reduced configuration; and
   a graft component attached to at least a portion of the self-expanding stent element and having an enlarged diameter less than the enlarged diameter of the self-expanding stent element in the deployed configuration;
   wherein in the deployed configuration, the self-expanding stent element exerts a radially expansive force to the graft component; the graft component having a yield strength greater than the radially expansive force and being configured to radially maintain the self-expanding stent element at the enlarged diameter of the graft component upon application of a second radially expansive force greater than the radially expansive force of the self-expanding stent element without the graft component enlarging in diameter by between more than about 0.1 mm and about 0.5 mm and the self-expanding stent includes apices that comprise intradoses and extradoses, and the graft component is configured to maintain compression of the intradoses of the apices.

2. The self-expanding endoprosthesis of claim 1, wherein the graft component is configured to resist plastic deformation upon application of the second radially expansive force.

3. The self-expanding endoprosthesis of claim 1, wherein the enlarged diameter of the self-expanding stent element is from 2% to 25% greater than the enlarged diameter of the graft component.

4. The self-expanding endoprosthesis of claim 1, wherein the graft component is a continuous structure attached to the self-expanding stent element forming a flow lumen of the self-expanding endoprosthesis.

5. The self-expanding endoprosthesis of claim 1, wherein the self-expanding stent element comprises a plurality of undulations formed by struts connecting the apices.

6. The self-expanding endoprosthesis of claim 5, wherein the graft component is configured to reduce tensile stress in the intradoses of the apices.

7. The self-expanding endoprosthesis of claim 6, wherein the self-expanding stent element and the graft component are reduced to the reduced configuration, and the intradoses of the apices remain in compression after expansion to the deployed configuration.

8. The self-expanding endoprosthesis of claim 1, wherein the self-expanding stent element is heat set to a manufactured diameter.

9. The self-expanding endoprosthesis of claim 8, wherein the manufactured diameter of the self-expanding stent element is from 15% to 20% greater than the enlarged diameter of the graft component.

10. The self-expanding endoprosthesis of claim 8, wherein the manufactured diameter of the self-expanding stent element is from approximately 1 mm to 3 mm greater than the enlarged diameter of the graft component.

11. The self-expanding endoprosthesis of claim 8, wherein the self-expanding stent element with a manufactured diameter of from 7 mm to 32 mm and the graft component has an expanded diameter of from 5 mm to 27 mm.

12. The self-expanding endoprosthesis of claim 11, wherein the graft component is configured to resist a radially expansive force greater than an outward force from the self-expanding stent element without expanding beyond the expanded diameter of the graft component, and the radially expansive force is between 3 atm and 6 atm.

13. The self-expanding endoprosthesis of claim 1, wherein the self-expanding stent element and the graft component are configured to compress to a reduced diameter from 4 French to 26 French.

14. The self-expanding endoprosthesis of claim 13, wherein the enlarged diameter of the graft component is from 2 mm to 53 mm.

15. A self-expanding endoprosthesis having a reduced configuration and a deployed configuration, the self-expanding endoprosthesis comprising:
    a self-expanding stent element having an enlarged diameter, the self-expanding stent element configured to exhibit plastic strain at the deployed configuration and in response to being reduced to the reduced configuration; and
    a graft component attached to at least a portion of the self-expanding stent element and having an enlarged diameter less than the enlarged diameter of the self-expanding stent element in the deployed configuration;
    wherein in the deployed configuration, the self-expanding stent element exerts a radially expansive force to the graft component; the graft component being configured to radially maintain the self-expanding stent element at the enlarged diameter of the graft component upon application of a second radially expansive force greater than the radially expansive force of the self-expanding stent element without the graft component enlarging in diameter by between more than about 0.1 mm and about 0.5 mm and the self-expanding stent includes apices that comprise intradoses and extradoses, and the graft component is configured to maintain compression of the intradoses of the apices.

* * * * *